United States Patent [19]

Ikada et al.

[11] Patent Number: 4,882,162

[45] Date of Patent: Nov. 21, 1989

[54] ARTIFICIAL SKIN

[75] Inventors: Yoshito Ikada; Shokyu Gen, both of Uji; Shigeo Ohi, Ayabe; Yosuke Urabe, Hiratsuka; Hiroyuki Kawashima, Ayase, all of Japan

[73] Assignee: Dow Corning Kabushiki Kaisha, Tokyo, Japan

[21] Appl. No.: 242,085

[22] Filed: Sep. 8, 1988

[30] Foreign Application Priority Data

Jun. 27, 1987 [JP] Japan ................................. 62-157500

[51] Int. Cl.$^4$ ............................................. A61L 15/04
[52] U.S. Cl. .................... 424/444; 424/423; 424/424; 128/156; 623/15; 606/213
[58] Field of Search ....................... 424/444, 424, 424; 623/15

[56] References Cited

U.S. PATENT DOCUMENTS

| | | | |
|---|---|---|---|
| 3,739,773 | 6/1973 | Schmitt et al. | 424/444 |
| 4,612,337 | 9/1986 | Fox, Jr. et al. | 424/423 |
| 4,703,108 | 10/1987 | Silver et al. | 424/94.64 |

*Primary Examiner*—Thurman K. Page
*Attorney, Agent, or Firm*—Allan O. Maki

[57] ABSTRACT

An artificial skin or bandage is formed from an elastomeric layer which is surfaced by a fibrous wound contacting layer which is first formed into a fabric and subsequently degraded by heat hydrolysis or other degradative treatment into a form which could no longer be formed into a fabric but which forms an ideal bioabsorbable wound contact surface in which damage to the newly formed, fragile epidermus is minimized.

11 Claims, No Drawings

ARTIFICIAL SKIN

FIELD OF THE INVENTION

The present invention relates to an artificial skin which is useful as a covering material for burn wounds, external wounds, etc., suffered by humans and other animals.

PRIOR ART

A number of materials are known from the art as an artificial skin or wound-covering material which may be temporarily used to cover a burn wound, external wound, etc., in order to prevent the loss of body fluids, in order to prevent bacterial infection, etc., and thus promote healing.

For example, Japanese patent application Laid Open [Kokai] No. 52-38796 [38,796/77] describes an artificial skin which consists of a silicone membrane and a collagen-mucopolysaccharide layer. When this artificial skin is placed on the wound surface, the growing epidermis and dermis, which are produced as healing develops by cells in the region underlying the wound, also penetrate into the collagen-mucopolysaccharide layer of the artificial skin, the collagen-mucopolysaccharide layer is ultimately replaced by the epidermis and dermis, and the upper silicone membrane layer then spontaneously exfoliates. However, this artificial skin suffers from the problem that its adhesion for the wound surface is not always entirely satisfactory.

A similar dressing is disclosed in U.S. Pat. No. 4,161,948 (Bielron) issued July 24, 1979. In the dressing shown in that patent a spongy or cellular resorbable wound contacting layer is disclosed. This construction also suffers from less than desired wound adhesion.

Japanese patent application Laid Open No. 55-125870 [125,870/80] describes a wound-covering material which consists of a silicone rubber membrane and nylon knit and which has collagen bonded to the knit. This wound-covering material does adhere satisfactorily to the wound surface because nascent epidermis also penetrates into the nylon knit. However, the nylon knit, which is attached to the silicone rubber substrate, becomes embedded in the epidermis, and when the silicone rubber membrane is peeled off after healing, the nylon knit ruptures the newly formed epidermis, causing bleeding, etc.

In order to solve these problems, research has been directed at the utilization of fibrous materials composed of bioabsorbable substances. However, fibrous materials prepared from currently known bioabsorbable substances generally have slow bioabsorption rates, with the result that they are not fully degraded by the organism within the usual period of healing and thus still remain even after healing. As a consequence, when peeled after the formation of new epidermis, there is again substantial risk of damaging the newly produced epidermis. Furthermore, a satisfactorily flexible artificial skin cannot be produced because these fibrous materials are very stiff.

A tactic thought to be effective for coping with these problems is the use of fibrous materials prepared from fine fibers. However, it is known in this regard that, due to the low strength of such fibers, it is difficult to develop the strength required for fibrous materials for artificial skin applications.

SUMMARY OF THE INVENTION

The present invention was developed based on the above circumstances, and has as its object the introduction of a sufficiently flexible artificial skin which uses fibrous material prepared from a bioabsorbable substance and with which, after the usual period of healing has elapsed, it will be possible reliably to peel off only the polymer support film without damaging newly formed epidermis.

The artificial skin of the present invention characteristically consists of a polymer support film and a fibrous material fixed on said polymer support film, wherein the fibrous material consists of bioabsorbable substance and the strength of said fibrous material has been reduced by means of a degradative treatment.

The fibrous material employed initially has a tensile strength sufficient to permit formation into a fabric using conventional methods, but subsequently is treated to reduce the tensile strength to a degree that would no longer permit such fabric formation but which possesses desirable properties for us as a wound contact surface. Knits and weaves prepared from bioabsorbable fibers and having strengths reduced by degradative treatment are preferred for the fibrous material. By means of this structure, one obtains an artificial skin having a satisfactory flexibility and strength, with the result that it satisfactorily adheres to the wound surface and does not separate during the period of healing up to the formation of nascent epidermis. Furthermore, because the fibrous material is prepared from a bioabsorbable substance, the fibrous material is absorbed by the tissues of the organism at the treated wound surface. This fibrous material, being weakened by a degradative treatment, is made flexible as a result, and as a consequence also has a high bioabsorption rate, with the result that it is fully degraded by the organism over the usual healing period, for example, between 2 and 4 weeks. This also results in a still further decline in its strength, and the polymer support film thus can be peeled off in a very satisfactory manner without damaging the newly formed epidermis.

DETAILED DESCRIPTION

The artificial skin of the present invention can be obtained by fixing a degradatively treated fibrous material composed of bioabsorbable substance on a polymer support film composed of polymeric substance, or by fixing the fibrous material composed of bioabsorbable substance on a polymer support film composed of polymeric substance and by then degradatively treating said fibrous material together with the polymer support film. As desired, the fibrous material may carry suitable biological preparations.

The polymer support film in the present case must (i) have a water permeability equivalent to or on the order of that of normal skin, (ii) have the flexibility necessary for the coverage of joints and other flexible body regions, (iii) have the strength necessary for attachment on the wound surface by, for example, sutures, etc., (iv) have a suitable integrity so peeling after healing may be carried out easily, (v) not be pyrogenic or antigenic, and (vi) be microbially resistant. Polymer support films which fully satisfy these requirements are preferred.

The materials comprising this polymer support film are exemplified by natural rubbers; synthetic rubbers such as silicone rubbers, urethane rubbers, fluororubbers, butadiene rubbers, styrene-butadiene rubbers, butyl rubbers, chloroprene rubbers, epichlorohydrin rubbers, etc.; polyethylene; polypropylene; polystyrene; polyvinyl chloride; polyvinyl acetate; polyvinyl alcohol; polyesters; fluororesins; etc. Among these, silicone elastomers and particularly silicone rubbers are preferred. Materials selected from the various silicone elastomers, such as, for example, peroxide-vulcanizing types, platinum-type catalyst-vulcanizing types, room temperature-curable types, etc., can be used to advantage. Use may also be made of so-called silicone adhesives or the blends or copolymers of such silicones with other organic polymers.

In concrete terms, the preceding is exemplified by commercially available silicones for medical applications from Dow Corning (USA) such as Dow Corning MDX 4-4210 elastomer, Silastic ® 382 elastomer, Dow Corning 891 adhesive, or Silastic ® Q7-4840 A/B elastomer.

Fibrous material composed of bioabsorbable substance is fixed on the aforementioned polymer support film. This fibrous material may be degradatively treated before or after its attachment on the polymer support film.

In general, the fibrous material composed of bioabsorbable substance is prepared by spinning a bioabsorbable polymer; however, it can be a mixed fiber of bioabsorbable polymer and nonbioabsorbable polymer. In the present sense, the bioabsorbable polymer is a substance which is degraded by the chemical activity of the organism's tissues and is absorbed by the organism when in contact with the organism's tissues. It is concretely exemplified by polyglycolic acid, polylactide, polydioxanone, polycaprolactone, glycolic acid-lactic acid copolymers (glycolide-lactide copolymers), collagen, polyamino acids, glycolide-caprolactone copolymers, amino acid-lactic acid copolymers, polylactic acid, lactic acid-caprolactone copolymers, chitin, chitosan, etc.

Concrete examples of such bioabsorbable polymer fibers are, among others, the commercially available Vicryl ® (glycolic acid-lactic acid copolymer from Ethicon, Inc.), PDS (polydioxanone from Ethicon, Inc.), Dexon ® (polyglycolic acid from Davis and Geck), etc.

The fibrous material composed of bioabsorbable substance as above can be used as the monofilament, fiber tow, knit or weave, that is, as the fiber's woven or knitted fabric, and a mesh-like weave or knit is particularly preferred.

The use of a fibrous material prepared from polyglycolic acid is particularly preferred in the present invention. In this case, for example, polyglycolic acid with an inherent viscosity of at least 1.0 is spun into yarn of no more than 50 denier, for example, 20 to 30 denier, by melt spinning; as desired the obtained yarn is stretched at 30 to 150 degrees Centigrade in order to increase the orientation; and this yarn is knitted or woven to afford the corresponding fabric. The texture of this knit or weave is not specifically restricted, and any texture may be used, such as weft-knitted fabrics such as single and double, warp-knitted fabrics such as tricot, plain weaves, twill weaves, etc.; however, weft-knitted textures are optimal from such standpoints as elasticity and flexibility. The density of the knit or weave is to fall within the range of 5 to 200 g/m2, preferably 5 to 50 g/m2, and particularly preferably 10 to 25 g/m2. Furthermore, the mesh should not be completely filled, but rather a porous material with regularly arranged openings (the mesh) is preferred.

The fiber must have the tensile strength of at least 50 gram per fiber to permit formation into a fabric. However, the strength of 60 or more grams per fiber is preferred in order to avoid knitting trouble. The preferred polyglycolic acid fiber is adjusted such that the strength is in the range of 90 to 168 grams per fiber (4.5 to 6.0 grams per denier and 20 to 28 denier per fiber). The fabric is said to be degraded generally to 30 to 60 percent by the treatment. That is to say, the fiber is to be degraded such that the strength is in the range of 30 to 67 grams per fiber. Accordingly the degraded fiber generally could not be knitted or woven.

The fibrous material consisting of bioabsorbable substance as described above may be subjected to the degradative treatment before or after attachment to the polymer support film. This degradative treatment functions to reduce the strength of the fibrous material by means of hydrolysis, thermal decomposition, oxidative degradation, etc. In concrete terms, it may be conducted by immersion of the fibrous material in hot water, through the action of high-pressure super heated steam, by a dry heat treatment, by exposure to radiation, etc. This will be established by selection of the various conditions of the degradative treatment from a consideration of the required properties, the nature of the fibrous material used, the fiber size, the texture, etc.

For example, when the fibrous material has been obtained from polyglycolic acid and is to be hydrolyzed by immersion in hot water, the fibrous material may be immersed for several tens of minutes to several hours at a hot water temperature of, for example, 80 to 100 degrees Centigrade. In a typical example in this case, the fibrous material is immersed in hot water at 100 degrees Centigrade for about 90 minutes. In the case of hydrolysis of such a fibrous material using high-pressure steam, treatment may last for several tens of minutes to one hour using steam with a temperature of 100 to 140 degrees Centigrade. In a typical example in this case, the fibrous material material is allowed to stand in steam at 120 degrees Centigrade for about 30 minutes. Dry heating treatment generally takes longer than a wet heating treatment. The former treatment at 160 to 170 degrees centigrade for 7 to 8 hours was found to correspond to the autoclave at 121 degrees centigrade for 30 minutes.

The fibrous material consisting of bioabsorbable substance suffers a partial loss in strength as a consequence of this degradative treatment, which causes the fibrous material to be less stiff and thus have a suitable flexibility. At the same time, its bioabsorption rate is elevated because the bioabsorbable substance has become more easily degraded by the organism. From this standpoint, the degradative treatment can be thought of as a bioabsorption-accelerating treatment.

In order to fix the fibrous material (before or after degradative treatment) on the polymer support film, one has recourse to methodologies in which the fibrous material is adhered on the already formed polymer support film through the use of an adhesive, for example, an acrylic or silicone adhesive, as well as methodologies in which the fibrous material is mounted on a polymer support film material which can be cured to afford the polymer support film and this polymer support film material is then cured under these conditions in order to unify the fibrous material with the polymer support film.

The fibrous material must be integrally fixed on the polymer support film to such a degree that the polymer support film will not separate from the treated wound surface during the healing period in which the artificial skin is applied and new epidermis grows.

With regard to the condition of the fibrous material fixed on the polymer support film, at least part of the fibers must be exposed on the external surface of the polymer support film or on the external surface of the adhesive when such is used. Furthermore, it is advantageous that the fibers forming the fibrous material project as loops from the external surface, or that the fibers on one surface of a mesh-like fibrous material be individually exposed.

No specific restriction obtains on the quantity or thickness of the fibrous material to be installed on the polymer support film, and the quantity (thickness) of the fibrous material, the status of the fibers which form the fibrous material, particularly the size and form of the fibers, and other factors are to be appropriately selected from a consideration of the type of bioabsorbable substances actually used in the fibrous material, the condition of the wound to be treated, and other conditions.

As desired, biological preparations can be supported on the aforesaid fibrous material composed of bioabsorbable substance. Concrete examples of biological preparations useful in this case are collagen, gelatin, fibrinogen, albumin, other proteins, hyaluronic acid, chondroitin sulfate, other mucopolysaccharides, lysine, aspartic acid, glycine, other amino acids, lecithin, etc. Among these, the use of collagen is particularly suitable.

Such biological preparations can be applied on the degradatively treated fibrous material, and the means for realizing this are not specifically restricted. Thus, the biological preparation can be supported on the fibrous material by means appropriately selected, based on a consideration of the properties of the biological preparation and other conditions, from methodologies such as, for example, spraying, immersion, etc. Furthermore, by applying the biological preparation to the fibrous material followed by a degradative treatment, it is possible to strengthen the bonding status by crosslinking the biological preparation to the fibrous material.

While no specific restriction obtains on the quantity of the biological preparation utilized the coating of such preparations generally is from several microns to approximately 100 microns on the fibrous material. Larger quantities of have been generally found to be uneconomical.

Furthermore, while it is generally sufficient to apply the biological preparation by means such as a simple coating of the fibrous material, a primer treatment, crosslinking reaction, or other specific means of attachment may generally be used.

With the use of an artificial skin having the above-described structure, nascent epidermis at the treated wound grows in such a way that it also penetrates into the fibrous material. Due to this, the artificial skin under consideration has a satisfactory adhesion for the wound surface, and will not separate from the treated wound until the wound has healed. Furthermore, although the fibrous material is composed of bioabsorbable substance, it nevertheless has a satisfactory flexibility as a consequence of the degradative treatment. Viewed from this aspect, the instant artificial skin has both a satisfactory adhesion for the wound surface as well as an enhanced absorption of the bioabsorbable substance. A satisfactory bioabsorption rate is thus obtained, and the fibrous material will be almost gone at the end of the typical healing period of 2 to 4 weeks. As a result, either the state of attachment between the fibrous material and the polymer support film is dissolved at the boundary of the fibrous material, or the force of attachment becomes very low. The polymer support film can then be reliably peeled by itself from the treated skin surface using very little force and without damaging newly formed epidermis.

As discussed above, degradative treatment of the fibrous material can be conducted under various conditions, for example, selecting the temperature or treatment time, which makes possible a modulation of the degree of degradative treatment of the fibrous material and ultimately provides for the production of fibrous material having a particular, desired bioabsorptivity. This makes possible the production of artificial skins having various application lives, and specifically an artificial skin having an optimal application life according to the condition of the wound to be treated.

By way of example, the application of a biological preparation to the fibrous material can serve, depending on the former's characteristics, to increase the compatibility or affinity for the organism's tissue, promote the growth of new epidermis, increase adhesion to the wound surface, etc. The instant fibrous material is a quite excellent carrier for biological preparations, and it is very easy to increase the contact area of such a biological preparation with the wound surface by supporting it in this manner on the fibrous material. Furthermore, in some cases one can anticipate that the strength of the entire artificial skin will be increased by supporting a biological preparation on the fibrous material.

EXAMPLES

The present invention will be explained in the following illustrative examples, but is not limited by them.

EXAMPLE 1

A support film material was prepared by coating a 40% Chlorothene ® dispersion of a platinum-type catalyst-vulcanizing silicone rubber, "Silastic ® Elastomer-Q7-4840 A/B", on a polyethylene terephthalate film in a quantity sufficient to give a thickness of 45 microns after curing.

A fibrous material (density=15 g/m2), which was obtained by converting a 22 denier polyglycolic acid fiber of 10 filaments into a mesh-like knit or weave, was hydrolyzed by exposure to high-pressure steam at 121 degrees Centigrade for 15 minutes in order to reduce its strength. This fibrous material was pressed into the silicone rubber layer of the support film material described above, and this was air-dried and then heated at 100 degrees Centigrade for 10 minutes in order to cure the silicone rubber layer and thus fix the fibrous material. A 0.3% aqueous solution of atelocollagen was then coated on the fibrous material by spraying, followed by drying at room temperature for 1 day to afford an artificial skin of the present invention (Sample 1).

EXAMPLE 2

An artificial skin according to the present invention was prepared as described in Example 1, with the exception that hydrolysis of the fibrous material as in Example 1 was carried out for 30 minutes (Sample 2).

EXAMPLE 3

An artificial skin according to the present invention was prepared as described in Example 1, with the exception that hydrolysis of the fibrous material as in Example 1 was carried out for 60 minutes (Sample 3).

COMPARISON EXAMPLE

A comparison artificial skin was prepared following the procedure described in Example 1 with the modification that the fibrous material of Example 1 was not subjected to the hydrolysis treatment (Comparison Sample 1).

The samples and comparison sample were sterilized with ethanol, and animal experiments were conducted as follows. The epidermis and dermis were removed from the back of a rabbit over a 15×20 mm area while preserving the cuniculus carnosus in order to form a whole skin-layer wound. The entire wound surface was covered with a sample or comparison sample (about 20×30 mm), which was pressed down and fixed by suturing to the surrounding skin. This was additionally protected with bandaging and plaster. After 9 days had elapsed after this, the external surface of the wound was inspected visually, and a tissue section was collected and stained with hematoxylin-eosin. The tissue reaction was then inspected using an optical microscope. The polymer support film was peeled off after 2 weeks or after 3 weeks, and similar inspections were carried out.

The following results were obtained.

AFTER NINE DAYS

Comparison Sample 1

(External surface)
Adhesion to the wound surface was relatively poor due to an unsatisfactory flexibility.
(Tissue picture)
A slight inflammatory response was observed.

Samples 1 to 3

(External surface)
Sample 1 had a very slight problem with adhesion to the wound surface, while Samples 2 and 3 presented good adhesion with the wound surface. Neither scar constriction nor deformation were observed on the wound surface.
(Tissue picture)
Almost no inflammatory response was observed and a good healing process was in evidence.

AFTER TWO WEEKS

Comparison Sample 1

(External surface)
Deformation was observed on the wound surface, although slight. The polymer support film was peeled with difficulty. Epidermis formation was observed, although it was peeled off together with the support film.
(Tissue picture)
Scar tissue morphology was observed.

Samples 1 to 3

(External surface)
Epidermis was completely formed on the wound. The polymer support films of Samples 2 and 3 could be peeled without resistance, and the external surface was completely healed. However, some force was required to peel off the polymer support film of Sample 1, and, although the formation of epidermis on the external surface was observed, a wound was present which was considered to have been generated by peeling. Furthermore, epidermal tissue adhered to the separated polymer support film.
(Tissue picture)
The wound was completely healed, good granulation formation was observed, and epidermis formation, although somewhat thick, was complete.

AFTER THREE WEEKS

Comparison Sample 1

(External surface)
Some force was required to peel off the polymer support film, although deformation of the wound was slight. While epidermis formation was observed, part of the tissue was peeled with the polymer support film.
(Tissue picture)
The wound was almost completely healed, good granulation formation was observed, and epidermis formaton, although somewhat thick, was complete.
Samples 1 to 3
(External surface)
Epidermis was completely formed on the wound, the polymer support films of Samples 1 to 3 could all be peeled without resistance, and the external surfaces were completely healed.
(Tissue picture)
The wound was completely healed, good granulation formation was observed, and epidermis formation, although somewhat thick, was complete.

EXAMPLE 4

An artificial skin was prepared by the method of Example 2, with the exception that a 0.1% aqueous solution of gelatin was used in place of the atelocollagen. This sample was used in animal experiments carried out as described above, and results similar to those for Example 2 were obtained.

What is claimed is:

1. Artificial skin characteristically consisting of a polymer support film and a woven or knitted fabric formed of fibrous material fixed on said polymer support film, wherein the fabric is prepared from bioabsorbable substance which has an initial strength when formed into a fabric of 90 to 168 grams per fiber and the strength of said fibrous material has been reduced to approximately 30 to 67 grams per fiber of degradative treatment.

2. Artificial skin as described in claim 1 wherein the fibrous material is a knit or a weave having the density of 5 to 200 grams per square meter, preferably 5 to 50 grams per square meter, with most preference of 10 to 25 grams per square meter.

3. Artificial skin as described in claim 2 wherein the fibrous material is prepared from a bioabsorbable substance selected from polyglycolic acid, polylactic acid and copolymers thereof.

4. Artificial skin as described in claim 1 wherein the fibrous material is prepared from polyglycolic acid.

5. Artificial skin as described in claim 3 wherein the polymer support film is prepared from silicone elastomer.

6. Artificial skin as described in claim 1 wherein the degradative treatment is carried out in hot water or in atmosphere of super heated steam in an autoclave.

7. Artificial skin as described in claim 6 wherein the degradative treatment is carried out in hot water at temperature of 80 to 100 degrees Centigrade.

8. Artificial skin as described in claim 6 wherein the degradative treatment is carried out in atmosphere of high pressure water vapor at 100 to 140 degrees Centigrade.

9. Artificial skin as described in claim 6 wherein the fibrous material has an initial tensile strength of at least 50 grams per fiber and the degradative treatment is carried out to the extent that the strength of the fibrous material is degraded to less than 60 percent of the initial strength thereof.

10. Artificial skin as described in claim 6 wherein degradative treatment is carried out after the fibrous material is fixed on the polymer support film.

11. Artificial skin as described in claim 1 wherein the fibrous material is treated with biologically acceptable-material as herein defined.

* * * * *